United States Patent
Horn

(10) Patent No.: US 11,214,569 B2
(45) Date of Patent: Jan. 4, 2022

(54) PRODRUGS OF QUINUCLIDINE RING-CONTAINING MUSCARINIC AGONISTS AND COMPOSITIONS AND METHODS THEREOF

(71) Applicant: Lenz Therapeutics, Inc., Rancho Santa Fe, CA (US)

(72) Inventor: Gerald Horn, Deerfield, IL (US)

(73) Assignee: LENZ THERAPEUTICS, INC., Rancho Santa Fe, CA (US)

( * ) Notice: Subject to any disclaimer, the term of this patent is extended or adjusted under 35 U.S.C. 154(b) by 0 days.

(21) Appl. No.: 16/700,088

(22) Filed: Dec. 2, 2019

(65) Prior Publication Data

US 2020/0181136 A1    Jun. 11, 2020

Related U.S. Application Data

(60) Provisional application No. 62/775,425, filed on Dec. 5, 2018.

(51) Int. Cl.
| | |
|---|---|
| C07D 453/02 | (2006.01) |
| C07F 9/59 | (2006.01) |
| C07F 9/6561 | (2006.01) |
| C07D 453/00 | (2006.01) |
| A61P 27/06 | (2006.01) |
| A61K 47/40 | (2006.01) |

(52) U.S. Cl.
CPC ............ *C07D 453/02* (2013.01); *A61K 47/40* (2013.01); *A61P 27/06* (2018.01); *C07D 453/00* (2013.01); *C07F 9/59* (2013.01); *C07F 9/6561* (2013.01)

(58) Field of Classification Search
CPC ....... C07D 453/02; C07D 453/00; C07F 9/59; C07F 9/6561
See application file for complete search history.

(56) References Cited

FOREIGN PATENT DOCUMENTS

JP    285607    *   2/1999

OTHER PUBLICATIONS

Stella (J. Pharmaceutical Sciences, 2010, 99(12), pp. 4755-4765).*
JP 2852607 (Google patent translation, downloaded May 19, 2021, pp. 1-6).*

* cited by examiner

*Primary Examiner* — Susanna Moore
(74) *Attorney, Agent, or Firm* — Wood, Phillips, Katz, Clark & Mortimer

(57) ABSTRACT

The present invention is directed to compounds of the formula

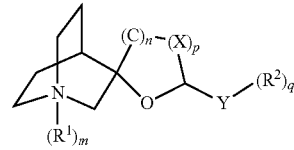

and salts or esters thereof. The present invention is further directed to ophthalmological compositions comprising a therapeutically effective amount of a compound of the present invention and one or more pharmaceutically acceptable excipients. The present invention is further directed to a methods of treating presbyopia or glaucoma or reducing hyperemia comprising administering to a patient in need thereof a therapeutically effective amount of a compound of the present invention.

22 Claims, No Drawings

PRODRUGS OF QUINUCLIDINE RING-CONTAINING MUSCARINIC AGONISTS AND COMPOSITIONS AND METHODS THEREOF

BACKGROUND OF THE INVENTION

Aceclidine is a muscarinic agonist with a quinuclidine ring (a tertiary nitrogen as part of a heterocyclic carbon ring) along with an acetyl ester bond to the heterocyclic ring two carbons away. Other muscarinic agonists with a quinuclidine ring include but are not limited to cevimeline, talsaclidine, and WAY-132983. In some cases, particularly for aceclidine, stability in solution is problematic for these drugs. The need to reconstitute any of the above drugs where stability in solution is an issue adds undesirable complexity in terms of patient compliance, adherence to sterile technique, which becomes essentially impossible, as well as other possible reformulation errors. For example, aceclidine has been commercially available for treatment of glaucoma as the salt, aceclidine HCl, for over forty years. During that time it has only been available as a lyophilized powder to be reconstituted by the user at the time of use.

In addition to its potential use as a glaucoma agent as in past years, aceclidine may have other applications as well, particularly for intraocular use, such as the treatment of presbyopia. Presbyopia is a normal and inevitable effect of ageing and is the first unmistakable sign for many in their forties that they are getting older. One study found that more than 1 billion people worldwide were presbyopic in 2005. This same study predicted that number to almost double by the year 2050. If everyone over the age of 45 is considered to be presbyopic, then an estimated 122 million people in the United States alone had presbyopia in 2010. As baby boomers reach the critical age, this number is only going to increase.

Presbyopia carries with it a stigma resulting from the limitation in ability to quickly function at many tasks requiring focusing at both distant and near points, which once occurred almost immediately. In the presbyopic patient, these tasks can be performed only by the use of eyeglasses, contact lenses or after undergoing invasive surgery. One such optical modification, the monovision procedure, can be executed with the use of glasses, contact lenses or even surgery. The monovision procedure corrects one eye for near focus and the other eye for distance focus. However, monovision correction is normally accompanied by loss of depth perception and distance vision particularly in dim light (e.g. night). Other surgical procedures that have been developed to relieve presbyopia include: (1) the implantation of intraocular lenses (INTRACOR®; registered trademark of Technolas Perfect Vision GMBH); (2) reshaping of the cornea (PresbyLASIK and conductive keratoplasty); (3) scleral band expansion; and (4) implantation of corneal inlays (Flexivue Microlens®; registered trademark of PresbiBio LLC, Kamra®; registered trademark of AcuFocus, Inc. and Vue+). Kamra® corneal inlays manufactured by AcuFocus work by inlaying a pinhole on the cornea to increase the depth of focus. A similar effect can be achieved with general miotic agents, such as pilocarpine (a non-selective muscarinic acetylcholine receptor agonist), carbachol (a non-selective muscarinic acetylcholine receptor agonist), and phospholine iodide (an acetylcholinesterase inhibitor). These general miotic agents trigger increased ciliary muscle contraction and induce accommodation of any remaining reserves, improving near vision at the expense of distance vision in individuals who still retain some accommodative function. While these general miotic agents also create improved depth of focus via a pinhole effect induced by pupillary miosis (i.e. constriction), to the degree accommodation occurs, the pinhole effect only partially offsets the induced accommodative myopia for distance. In some cases, such as with pilocarpine or carbachol, the induced accommodation may create up to 5 diopters or more of induced myopia resulting in induced myopia causing blurred distance vision generally and during shift of the focal point from distance to near. These general miotic agents also cause substantial redness, severe nasal congestion and create ciliary muscle spasms, which commonly induces discomfort that can be severe and long-lasting. In extreme cases, such ciliary muscle spasms can result in retinal detachment.

Aceclidine provides enhanced presbyopic reversal while causing little to no side effects. However, aceclidine, like many quinuclidine-ring containing muscarinic agonists has a poor shelf-life and is difficult to solubilize. Thus, there is a need in the art for stable solubilized forms of aceclidine and other quinuclidine-ring containing muscarinic agonists.

SUMMARY OF THE INVENTION

The present invention provides derivatives of quinuclidine-ring containing compounds.

The present invention further provides stable prodrugs of quinuclidine-ring containing muscarinic agonists.

In another embodiment, the present invention provides an ophthalmological composition comprising a therapeutically effective amount of a compound of the present invention and one or more pharmaceutically acceptable excipients.

In another embodiment, the present invention provides an ophthalmological composition comprising a therapeutically effective amount of a compound of the present invention wherein the pH of the composition is at least 3 log units less than the pKa of the compound.

In another embodiment, the present invention provides an ophthalmological composition comprising a therapeutically effective amount of a compound of the present invention and a cyclodextrin wherein the pH of the composition is at least 3 log units less than the pKa of the compound.

In another embodiment, the present invention provides an ophthalmological composition comprising a therapeutically effective amount of a compound of the present invention and a cyclodextrin selected from an alpha-cyclodextrin, a beta-cyclodextrin and a gamma-cyclodextrin wherein the pH of the composition is at least 3 log units less than the pKa of the compound.

In another embodiment, the present invention provides a method of treating presbyopia or glaucoma comprising administering to a patient in need thereof a therapeutically effective amount of a compound of the present invention.

In another embodiment, the present invention provides a method of reducing hyperemia comprising administering to a patient in need thereof a therapeutically effective amount of a compound of the present invention.

In a preferred embodiment, the present invention provides a compound of formula (I)

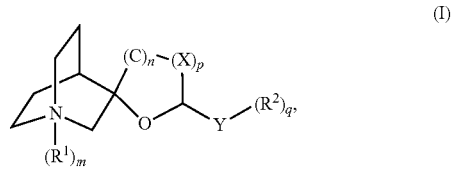

wherein:

m, n, p and q are each independently an integer of 0 or 1;

X is C or S;

Y is C, N, O, S or

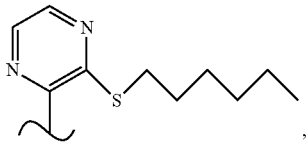

, wherein when Y is C an alkyne is optionally formed, when Y is N an imine or an oxime is formed, and when Y is O a carbonyl is formed;

$R^1$ has the formula —CH—$R^3$—O—$R^4$;

$R^2$ is an optionally substituted imine or oxime;

$R^3$ is selected from H or an alkyl; and $R^4$ is selected from a phosphate, a sulfate, a trifluoroacetate or a polar amino acid, or any pharmaceutically acceptable salt, ester or prodrug thereof.

In a more preferred embodiment the present invention provides a compound of formula (I)

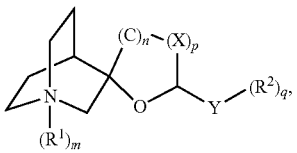

(I)

wherein:

m and p are 1;

n and q are 0;

X is C;

Y is O wherein a carbonyl is formed;

$R^1$ has the formula —CH—$R^3$—O—$R^4$;

$R^3$ is selected from H or an alkyl; and $R^4$ is selected from a phosphate, a sulfate or a polar amino acid, or any pharmaceutically acceptable salt, ester or prodrug thereof.

In another more preferred embodiment, the present invention provides a compound of formula (I)

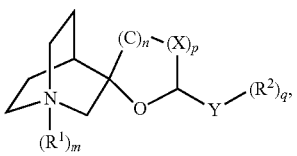

(I)

wherein:

m, and n are 0;

p and q are 1;

X is C;

Y is N wherein an imine or an oxime is formed;

$R^2$ is selected from

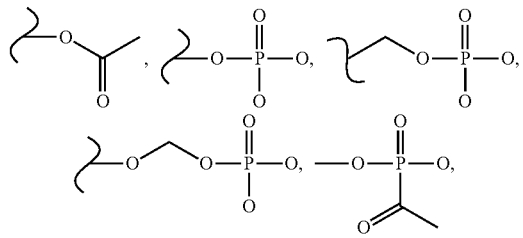

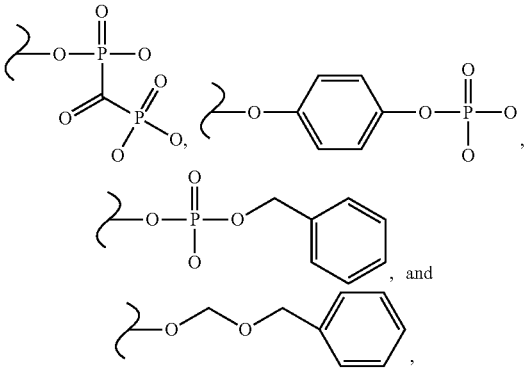

, and or any pharmaceutically acceptable salt, ester or prodrug thereof.

DETAILED DESCRIPTION OF THE INVENTION

Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used herein, the terms "optional" or "optionally" means that the subsequently described event or circumstance can or cannot occur, and that the description includes instances where said event or circumstance occurs and instances where it does not.

As used herein, the term "composition" is intended to encompass a product comprising the specified ingredients in the specified amounts, as well as any product which results, directly or indirectly, from a combination of the specified ingredients in the specified amounts.

The terms "treating" and "treatment" refer to reversing, alleviating, inhibiting, or slowing the progress of the disease, disorder, or condition to which such terms apply, or one or more symptoms of such disease, disorder, or condition.

As used herein, the term "effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, an "effective amount" will depend upon the context in which it is being administered. An effective amount may be administered in one or more prophylactic or therapeutic administrations.

As used herein, the term "pharmaceutically acceptable" describes a material that is not biologically or otherwise undesirable, i.e., without causing an unacceptable level of undesirable biological effects or interacting in a deleterious manner.

As used herein the term "patient" refers but is not limited to a person or other animal.

As used herein, the term "substituted" is contemplated to include all permissible substituents of organic compounds. In a broad embodiment, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain embodiments, unless expressly indicated to the contrary, individual substituents can be further optionally substituted (i.e., further substituted or unsubstituted).

As used herein, the term "X" refers to a carbon or a sulphur.

As used herein, the term "Y" refers to a carbon, a nitrogen, an oxygen, a sulphur or

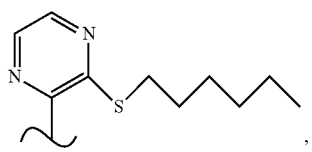

wherein when Y is carbon an alkyne is optionally formed, when Y is nitrogen an imine is formed, and when Y is oxygen a carbonyl is formed.

As used herein, the term $R^1$ refers to the formula —CH—$R^3$—O—$R^4$.

As used herein, the term $R^2$ refers to an optionally substituted imine or oxime. In a preferred embodiment $R^2$ is selected from

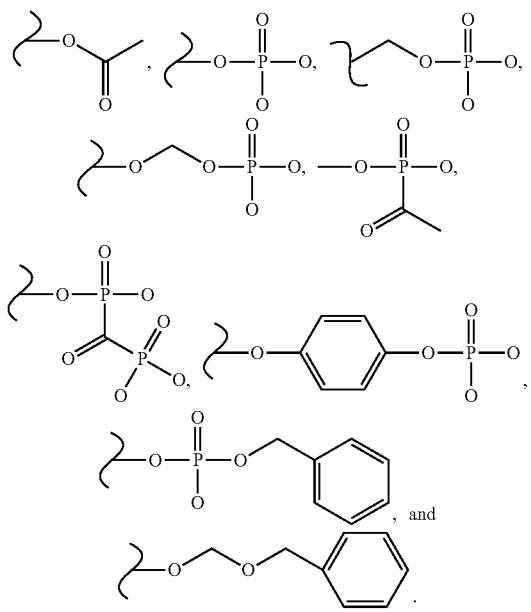

As used herein, the term $R^3$ refers to a hydrogen or an alkyl.

As used herein, the term $R^4$ refers to a phosphate, a sulfate, a trifluoroacetate or a polar amino acid.

As used herein, term "alkyl" is a branched or straight-chain alkyl consisting of a saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or straight-chained. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, thiol, a phosphate or a sulfate.

As used herein, the term "carbonyl" refers to the formula C=O,

As used herein, the term "alkyne" refers to the formula C≡C,

As used herein, the term "polar amino acid" refers to arginine, asparagine, aspartate, cysteine, glutamate, glutamine, histidine, lysine, serine or threonine.

As used herein, the term "imine" refers to a group of the formula C=N—Y—R', wherein R' is a hydrogen, an alkyl, an acyl, an alkoxy, an acyloxyalkyl, an alkoxycarbonyl, a carbamoyl, a cycloalkyl, a heteroalicyclic, an aryl, a heteroaryl, an N-Mannich base, an imidazolidinone, an oxazolidinone, a phosphate or a sulfate and wherein Y is selected from a bond, $CH_2$, CO, $PO_2$—CO, and $PO_3$—$CH_2$, wherein CO denotes a carbonyl.

As used herein, the term "oxime" refers to a group of the formula C=N—O—Y—R', wherein R' is a hydrogen, an alkyl, an acyl, an alkoxy, an acyloxyalkyl, an alkoxycarbonyl, a carbamoyl, a cycloalkyl, a heteroalicyclic, an aryl, a heteroaryl, an N-Mannich base, an imidazolidinone, an oxazolidinone, a phosphate or a sulfate wherein Y is selected from a bond, $CH_2$, CO, $PO_2$—CO, and $PO_3$—$CH_2$, wherein CO denotes a carbonyl.

As used herein, the term "sulfate" refers to a group of the formula

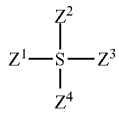

wherein each of $Z^1$, $Z^2$, $Z^3$ and $Z^4$ are independently selected from a bond, a hydrogen, a carbon and an oxygen.

As used herein, the term "phosphate" refers to a group of the formula

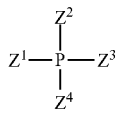

wherein each of $Z^1$, $Z^2$, $Z^3$ and $Z^4$ are independently selected from a bond, a hydrogen, a carbon and an oxygen.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain embodiments, unless expressly indicated to the contrary, individual substituents can be further optionally substituted (i.e., further substituted or unsubstituted).

Suitable monovalent substituents on a substitutable carbon atom of an "optionally substituted" group are each independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)$ $C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched)alkylene)O—$N(R°)_2$; or —$(C_{1-4}$ straight or branchedalkylene)C(O)O—$N(R°)_2$, wherein each $R°$ may be substituted as defined below and is independently hydrogen, $C_{1-6}$aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^●$ (or the ring formed by taking two independent occurrences of $R^●$ together with their intervening atoms), are independently halogen, —$(CH_2)_{0-2}R^●$, —(halo$R^●$), —$(CH_2)_{0-2}OH$, —$(CH_2)_{0-2}OR^●$, —$(CH_2)_{0-2}CH(OR^●)_2$; O(halo$R^●$), —CN, —$N_3$, —$(CH_2)_{0-2}C(O)R^●$, —$(CH_2)_{0-2}C(O)OH$, —$(CH_2)_{0-2}C(O))OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, $C(O)SR^●$, —$(C_{1-4}$ straight or branched alkylene)$C(O)OR^●$, or —$SSR^●$ wherein each $R^●$ is unsubstituted or where preceded by "halo" is substituted only with one or more halogens, and is independently selected from C1-4 aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR*_2$, =$NNHC(O)R*$, =$NNHC(O)OR*$, =$NNHS(O)_2R*$, =$NR*$, =$NOR*$, —$O(C(R*_2))_{2-3}O$—, or —$S(C(R*_2))_{2-3}S$—, wherein each independent occurrence of $R*$ is selected from hydrogen, C1-6 aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR*2)2-3O$—, wherein each independent occurrence of $R*$ is selected from hydrogen, C1-6 aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R*$ include halogen, —$R^●$, (halo$R^●$), OH, —OR□, —O(halo$R^●$), —CN, —C(O)OH, —C(O)OH, —C(O)$OR^●$, —$NH_2$, —NHR□, —$NR^●_2$, or —$NO_2$, wherein each $R^●$ is unsubstituted or where preceded by "halo" is substituted only with one or more halogens, and is independently C1-4 aliphatic, —$CH_2Ph$, —$O(CH_2)0-1Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)$CH_2$C(O)R†, —$S(O)_2$R†, $S(O)_2$NR†$_2$, —C(S)NR†$_2$, —C(NH)NR†2, or —N(R†)$S(O)_2$R†; wherein each R† is independently hydrogen, C1-6 aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R$^●$, (haloR$^●$), —OH, —OR$^●$, —O(haloR$^●$), —CN, —C(O)OH, —C(O)OR$^●$, —NH$_2$, —NHR$^●$, —NR$^●_2$, or NO2, wherein each R$_□$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as 2 H, 3 H, 13 C, 14 C, 15 N, 18 O, 17 O, 35 S, 18F and 36 Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as 3 H and 14 C are incorporated, are useful in drug and/or substrate tissue distribution assays. Tritiated, i.e., 3 H, and carbon-14, i.e., 14 C, isotopes are particularly preferred for their ease of preparation and detectability. Further, substitution with heavier isotopes such as deuterium, i.e., 2 H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

The term "prodrug" or "prodrugs" refers to compounds, including monomers and dimers of the compounds of the invention, which have cleavable groups and become under physiological conditions compounds which are pharmaceutically active in vivo.

As used herein "ester" or "esters" is represented by the formula —OC(O)A$^1$ or —C(O)OA$^1$, where A$^1$ can be alkyl, cycloalkyl, alkenyl, cycloalkenyl, alkynyl, cycloalkynyl, aryl, a heteroaryl group or other suitable substituent.

As used herein "salt" or "salts" refers to those salts which retain the biological effectiveness and properties of the parent compounds and which are not biologically or otherwise harmful at the dosage administered. Salts of the compounds of the present inventions may be prepared from inorganic or organic acids or bases.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, malic acid, sulphuric acid and phosphoric acid and such organic acids as oxalic acid, malic acid, maleic acid, methanosulfonic acid, succinic acid and citric acid. Preferred acid addition salts are prepared from methanosulfonic acid, malic acid and phosphoric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Compounds of the Invention

In a preferred embodiment, aceclidine prodrugs of the present invention include:

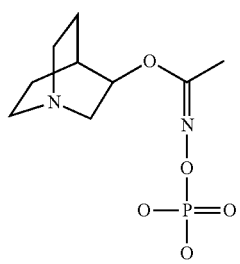 [SMILES: CC(=NOP(=O)(O)O)OC1CN2CCC1CC2]

aceclidine oxime substituted phosphate ester with an estimated log P of –0.076 and an estimated half life of 5 minutes in borate buffer (pH 7.4) and 30 minutes in acetate buffer (pH 5.0);

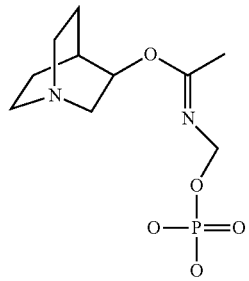 [SMILES: C/C(=N\COP(=O)(O)O)OC1CN2CCC1CC2]

estimated log P of –0.064,

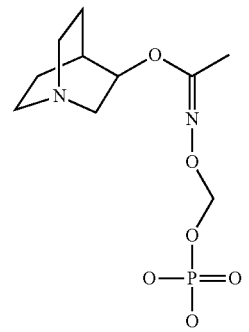 [SMILES: CC(=NOCOP(=O)(O)O)OC1CN2CCC1CC2]

estimated log P of –0.105,

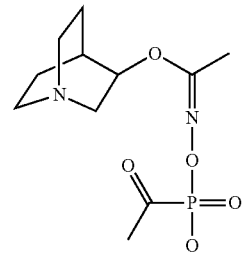 [SMILES: CC(=O)P(=O)(O)ON=C(C)OC1CN2CCC1CC2]

aceclidine oxime substituted carboxylic phosphate ester with an estimated log P of 0.495;

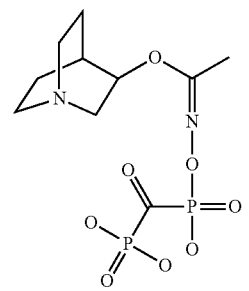 [SMILES: CC(=NOP(=O)(O)C(=O)P(=O)(O)O)OC1CN2CCC1CC2]

aceclidine oxime substituted phosphate carbonyl phosphate with an estimated log P of −1.152;

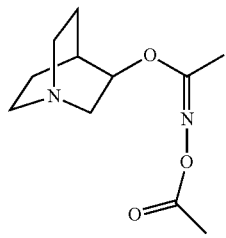 [SMILES: CC(=O)ON=C(C)OC1CN2CCC1CC2]

estimated log P of 1.295;

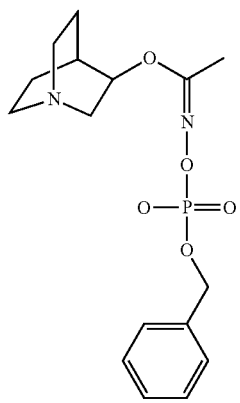 [SMILES: CC(=NOP(=O)(O)OCc1ccccc1)OC1CN2CCC1CC2]

estimated log P of 1.836;

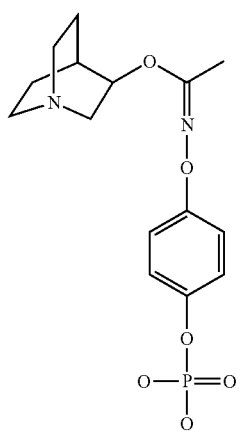 [SMILES: CC(=NOc1ccc(OP(=O)(O)O)cc1)OC1CN2CCC1CC2]

aceclidine nitroxamine benzylphosphate with an estimated log P of 1.654; and

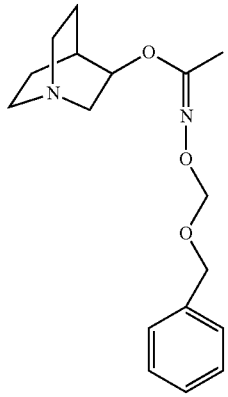 [SMILES: CC(=NOCOCc1ccccc1)OC1CN2CCC1CC2]

estimated log P of 2.773,

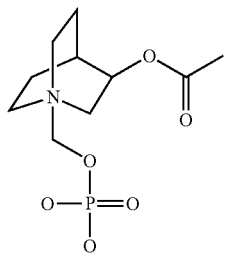

phosphono oxylmethyl aceclidine with an estimated pKa of 9.22, or any pharmaceutically acceptable salt, ester or prodrug thereof.

For topical aceclidine a short onset is normally desired, such as for application of a miotic effect to improve depth of focus for near vision. The selection of a phosphate prodrug moiety results in the shortest onset due to having the shortest reversion time to aceclidine and is most desired. The selection of a sulfate or amino acid prodrug moiety, for example, is much more stable and would result in a much later onset due to the longer reversion time to aceclidine. Due to the alteration in structure, the prodrug is prophetically predicted to eliminate the hyperemia normally seen in aceclidine dissolved in aqueous solutions.

In another preferred embodiment, quinuclidine ring-containing muscarinic agonist prodrugs of the present invention include:

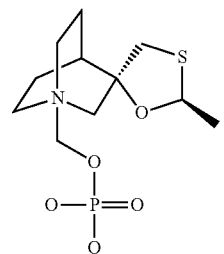

phosphono oxymethyl cevimeline with an estimated pKa of 8.59,

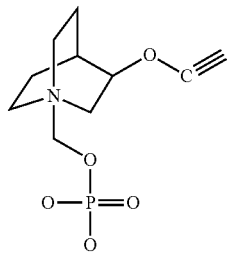

phosphono oxymethyl talsaclidine with an estimated pKa of 9.45 and

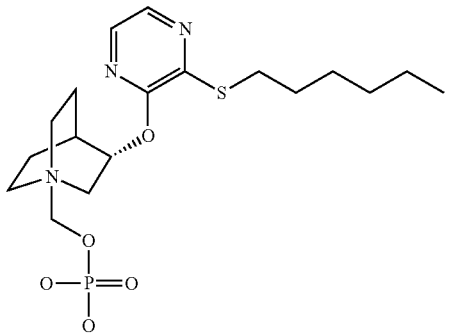

phosphono oxymethyl WAY-132983.

Methods of making the compounds of the present invention are within the skill of a person skilled in the relevant art.

Compositions of the Invention

Compositions of the present invention include excipients not limited to surfactants, viscosity enhancers, tonicity adjustors, osmolality modifiers, solubility enhancers, preservatives and buffers.

Surfactants suitable for the present invention include, but are not limited to, nonionic, cationic and/or anionic surfactants. Specific surfactants include cyclodextrins, polyoxyl alkyls, poloxamers or combinations thereof. Further, substitution of other surfactants compatible with ophthalmic use allows for similar composition advantages, which may included but is not limited to one or more of a nonionizing surfactant such as poloxamer, Poloxamer 188, Poloxamer 407, Polysorbate 20, Polysorbate 80, ionically charged (e.g. anionic) beta-cyclodextrins with or without a butyrated salt (Captisol®; (sulfobutylether β-cyclodextrin, Captisol is a registered trademark of Cydex Pharmaceuticals), 2-hydroxypropyl beta cyclodextrin ("HPβCD"), Polyoxyl 35 stearate, Polyoxyl 40 castor oil and Polyoxyl 40 hydrogenated castor oil, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxol, polyoxyl stearate, nonoxynol, octyphenol ethoxylates, nonyl phenol ethoxylates, capryols, lauroglycol, PEG such as PEG400, Brij® 35(polyoxyethyleneglycol dodecyl ether; Brij is a registered trademark of Uniqema Americas LLC), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris(hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl) methyl-2-aminoethane sulfonic acid (TES), 2-Amino-2-hydroxymethyl-propane-1,3-diol (Tris), tyloxapol, Span® 20-80 (sorbitan monolaurate, sorbitan monopalmitate, sorbitan monostearate, and sorbitan monooleate; Span is a registered trademark of Uniqema Americas Inc.), Tween® 20 (Tween is a registered trademark of Uniqema Americas LLC), Tween® 80, Labrasol® (caprylocaproyl macrogol-8 glycerides; Labrasol is a registered trademark of Gattefosse SAS). Surfactants of the present invention can be at a concentration from about 0.01% to about 99% w/v, preferably from about 1% to about 30% w/v.

Solubility enhancers (i.e. solvents) suitable for the present invention include, but are not limited to, glycofurol (a.k.a. tetraglycol and tetraethylene glycol), dimethyl sulfoxide ("DMSO"), vitamin E TPGS (d-alpha tocopheryl polyethylene glycol 1000 succinate), dimethyl sorbide ("DMI"), ethyl acetate, acetonitrile, ethyl alcohol, alcohols, polyols, amides, esters, polyethylene glycol, propylene glycol, propylene glycol ethers, polysorbates, poloxamers, cyclodextrins, Span 20-80, dimethyl isosorbide, isopropyl myristate oil and complexing agents such as cyclodextrins and nicotinamide or a combination thereof.

Viscosity enhancers suitable for the present invention include, but are not limited to, carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxyethyl cellulose, or hydroxyethyl cellulose, hyaluronic acid, dextran, polyethylene glycol, polyvinyl alcohol, polyvinyl pyrrolidone, gellan, carrageenan, alignic acid, carboxyvinyl polymer or combinations thereof.

A tonicity adjustor can be, without limitation, a salt such as sodium chloride ("NaCl"), potassium chloride, mannitol or glycerin, or another pharmaceutically or ophthalmically acceptable tonicity adjustor. In certain embodiments the tonicity adjustor is 0.3% w/v glycerin. In other embodiments the tonicity adjustor is 0.037% w/v NaCl.

Glycofurol is formulated in the topical compositions of the present invention due to its percutaneous absorption ability and its "generally recognized as safe" (GRAS) status in the Handbook of Pharmaceutical Excipients.

Osmolality modifiers suitable for the present invention include, but are not limited to, mannitol, sorbitol, glycerol and a combination thereof.

Preservatives that can be used with the present invention include, but are not limited to, benzalkonium chloride (BAK), chlorobutanol, thimerosal, phenylmercuric acetate, disodium ethylenediaminetetraacetic acid, phenylmercuric nitrate, perborate or benzyl alcohol. In a preferred embodiment the preservative is BAK at a concentration of about 0.001% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, citric acid buffers, phosphate buffers and borate buffers. It is understood that acids or bases can be used to adjust the pH of the composition as needed, preferably of 1 to 10 mM concentration, and more preferably about 5 mM. In a preferred embodiment the pH is from about 4.0 to about 8.0, in a more preferred embodiment the pH is from about 7.0 to about 7.5 in a most preferred embodiment the pH is about 5.0 or 7.4.

In a more preferred embodiment, the present invention includes storing compounds of the invention at a pH of at least 3 log units lower than the pKa of the compound. For example, the pKa of phosphono oxylmethyl aceclidine is about 9.22 wherein the preferred pH range for stability in solution is a pH of 6.22, more preferred 5.72 and most preferred less than or equal to 5.22.

TABLE 1

| pH vs. Solution Stability of Phosphono Oxylmethyl Prodrugs. | | | | | | | | | |
|---|---|---|---|---|---|---|---|---|---|
| Drug (pKa) | Cevimiline (8.59) | | | Talsaclidine (9.45) | | | Aceclidine (9.22) | | |
| pH of solution | 6.59 | 5.59 | 4.59 | 7.45 | 6.45 | 5.45 | 7.22 | 6.22 | 5.22 |
| Solubility | Poor | Fair | Best | Poor | Fair | Best | Poor | Fair | Best |

In an even more preferred embodiment, the present invention includes the addition of an alpha, beta or gamma-cyclodextrin to further enhance stability. Not wishing to be held to a particular theory, the selection of the most preferred cyclodextrin is dependent upon the size of the drug/prodrug in proportion to the nonpolar cavity of the cyclodextrin.

What is claimed is:

1. A compound of formula (I),

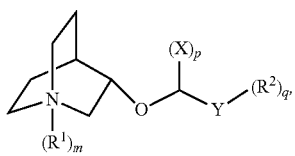

(I)

wherein:
m is an integer of 0 or 1, when m is 0, $R^1$ is absent;
p is an integer of 0 or 1, when p is 0, X is a bond;
q is an integer of 0 or 1, when q is 0, $R^2$ is a bond;

X is $CH_3$;
Y is C, N, O, S or

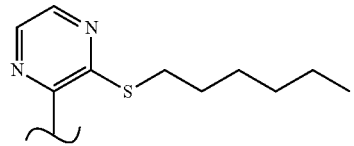

wherein when Y is C, an alkyne is optionally formed, when Y is N, an optionally substituted imine or an oxime is formed together with $R^2$, and when Y is O, a carbonyl is formed;

$R^1$ has the formula $-CH_2-R^3-O-R^4$, $R^2$ is selected from

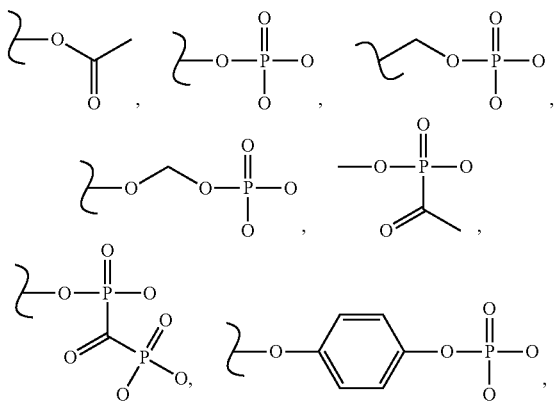

with the proviso when Y is N and an oxime is formed together with $R^2$, then $R^2$ is OH; or
when Y is

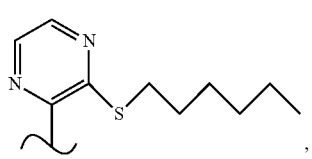

R² is H;

R³ is selected from a bond between CH₂ and O of R¹ or an alkyl; and

R⁴ is selected from a phosphate, a sulfate, a trifluoroacetate or a polar amino acid, or any pharmaceutically acceptable salt or ester thereof.

2. The compound of claim 1 wherein:

m is 0;

p and q are 1;

X is C; and

Y is N, wherein Y forms an optionally substituted imine or an oxime with R².

3. The compound of claim 2 selected from

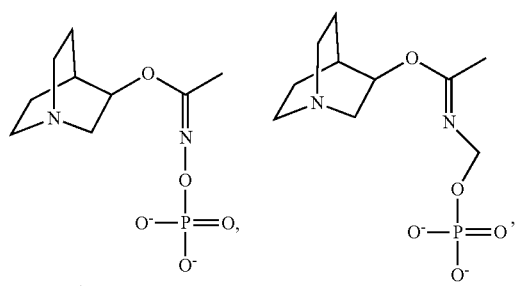

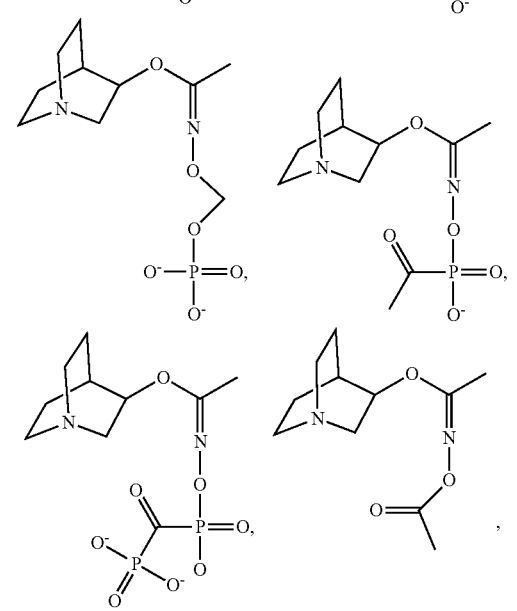

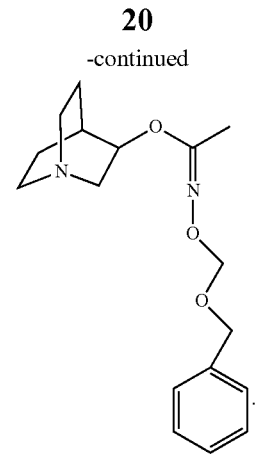

4. The compound of claim 1 wherein:

m and p are 1;

q is 0;

X is C; and

Y is O.

5. The compound of claim 1 selected from

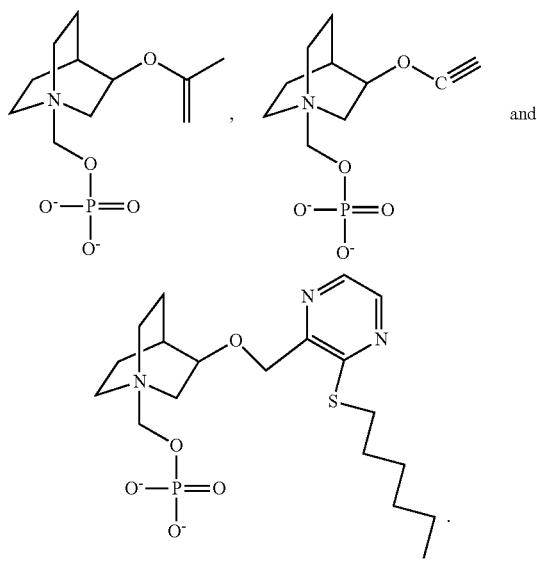

6. A compound of formula II,

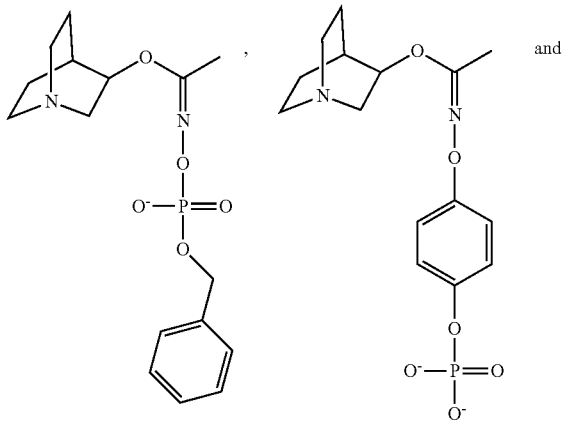

(II)

or a pharmaceutically acceptable salt or ester thereof.

7. A compound of formula (III),

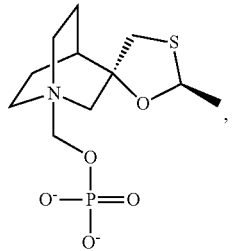

(III)

or a pharmaceutically acceptable salt or ester thereof.

8. An ophthalmological composition comprising a therapeutically effective amount of a compound of claim 1.

9. The composition of claim 8 further comprising a cyclodextrin.

10. The composition of claim 9 wherein the cyclodextrin is selected from an alpha-cyclodextrin, a beta-cyclodextrin and a gamma-cyclodextrin.

11. A method of treating presbyopia or glaucoma comprising administering to a patient in need thereof a therapeutically effective amount of a compound of claim 1.

12. A method of reducing hyperemia comprising administering to a patient in need thereof a therapeutically effective amount of a compound of claim 1.

13. An ophthalmological composition comprising a therapeutically effective amount of a compound of claim 6.

14. The composition of claim 13 further comprising a cyclodextrin.

15. The composition of claim 14 wherein the cyclodextrin is selected from an alpha-cyclodextrin, a beta-cyclodextrin and a gamma-cyclodextrin.

16. A method of treating presbyopia or glaucoma comprising administering to a patient in need thereof a therapeutically effective amount of a compound of claim 6.

17. A method of reducing hyperemia comprising administering to a patient in need thereof a therapeutically effective amount of a compound of claim 6.

18. An ophthalmological composition comprising a therapeutically effective amount of a compound of claim 7.

19. The composition of claim 18 further comprising a cyclodextrin.

20. The composition of claim 19 wherein the cyclodextrin is selected from an alpha-cyclodextrin, a beta-cyclodextrin and a gamma-cyclodextrin.

21. A method of treating presbyopia or glaucoma comprising administering to a patient in need thereof a therapeutically effective amount of a compound of claim 7.

22. A method of reducing hyperemia comprising administering to a patient in need thereof a therapeutically effective amount of a compound of claim 7.

\* \* \* \* \*